United States Patent
Roberts et al.

(10) Patent No.: US 10,512,733 B2
(45) Date of Patent: Dec. 24, 2019

(54) SAFETY DEVICE FOR A PRE-FILLED SYRINGE AND INJECTION DEVICE

(71) Applicant: Sanofi-Aventis Deutschland GMBH, Frankfurt am Main (DE)

(72) Inventors: Gareth Roberts, Wrexham (GB); Chris Ward, Prestatyn Dennbigshire (GB); Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 16/352,398

(22) Filed: Mar. 13, 2019

(65) Prior Publication Data

US 2019/0209784 A1 Jul. 11, 2019

Related U.S. Application Data

(63) Continuation of application No. 15/973,059, filed on May 7, 2018, which is a continuation of application No. 15/097,712, filed on Apr. 13, 2016, now Pat. No. 9,962,499, which is a continuation of application No. 13/807,043, filed as application No. (Continued)

(30) Foreign Application Priority Data

Jul. 2, 2010 (EP) .................................. 10168319

(51) Int. Cl.
*A61M 5/32* (2006.01)

(52) U.S. Cl.
CPC .......... *A61M 5/3202* (2013.01); *A61M 5/326* (2013.01); *A61M 5/3245* (2013.01); *A61M 5/3271* (2013.01); *A61M 5/3272* (2013.01); *A61M 5/3204* (2013.01); *A61M 5/3287* (2013.01); *A61M 2005/3268* (2013.01)

(58) Field of Classification Search
CPC .. A61M 5/3202; A61M 5/3245; A61M 5/326; A61M 5/3271; A61M 5/3272
USPC .......................................................... 604/198
See application file for complete search history.

(56) References Cited

U.S. PATENT DOCUMENTS 3,702,608 A * 11/1972 Tibbs .................. A61M 5/2033
604/136
4,232,669 A 11/1980 Nitshke
4,270,537 A 6/1981 Romaine
(Continued)

FOREIGN PATENT DOCUMENTS

EP 2531244 12/2012
WO WO 2011/092518 8/2011

*Primary Examiner* — Phillip A Gray
(74) *Attorney, Agent, or Firm* — Fish & Richardson P.C.

(57) ABSTRACT

According to the invention a safety device for a pre-filled syringe comprises a substantially cylindrical and hollow support body and a hollow needle shield slideably arranged relative to the support body. The support body comprises at least one resilient arm and the hollow needle shield or a needle shield assembly comprises at least one curved actuation ramp. The curved actuation ramp protrudes in a lateral direction (L) perpendicular to a central axis (A) of the safety device. The curved actuation ramp comprises a first lateral dimension (L1) at a proximal end of the needle shield and a second lateral dimension (L2) exceeding the first lateral dimension (L1) at a distal end of the needle shield. The resilient arm engages the curved actuation ramp when the needle shield is slid relative to the support body.

30 Claims, 5 Drawing Sheets

Related U.S. Application Data

PCT/EP2011/060320 on Jun. 21, 2011, now Pat. No. 9,314,574.

(56) References Cited

U.S. PATENT DOCUMENTS

| | | |
|---|---|---|
| 5,271,527 A | 12/1993 | Haber et al. |
| 5,295,965 A | 3/1994 | Wilmot |
| 5,300,039 A | 4/1994 | Poulson |
| 5,312,366 A | 5/1994 | Vailancourt |
| 5,378,233 A | 1/1995 | Haber et al. |
| 5,527,294 A | 6/1996 | Weatherford et al. |
| 5,540,664 A | 7/1996 | Wyrick |
| 5,746,215 A | 5/1998 | Manjarrez |
| 5,795,336 A | 8/1998 | Romano et al. |
| 5,873,856 A | 2/1999 | Hjertman et al. |
| 5,938,642 A | 8/1999 | Burroughs et al. |
| 5,957,896 A | 9/1999 | Bendek et al. |
| 6,183,446 B1 | 2/2001 | Jeanbourquin |
| 6,221,046 B1 | 4/2001 | Burroughs et al. |
| 6,235,004 B1 | 5/2001 | Steenfeldt-Jensen et al. |
| 6,726,657 B1 | 4/2004 | Dedig et al. |
| 6,743,205 B2 | 6/2004 | Nolan et al. |
| 6,805,686 B1 | 10/2004 | Fathallah et al. |
| 6,808,507 B2 | 10/2004 | Roser |
| 6,986,760 B2 | 1/2006 | Giambattista et al. |
| 7,011,649 B2 | 3/2006 | De La Serna et al. |
| 7,074,211 B1 | 7/2006 | Heiniger et al. |
| 7,112,187 B2 | 9/2006 | Karlsson |
| 7,201,740 B2 | 4/2007 | Crawford |
| 7,252,651 B2 | 8/2007 | Haider et al. |
| 7,361,160 B2 | 4/2008 | Hommann et al. |
| 7,585,287 B2 | 9/2009 | Bresina et al. |
| 7,744,565 B2 | 6/2010 | Heiniger et al. |
| 7,918,824 B2 | 4/2011 | Bishop et al. |
| 8,172,810 B2 | 5/2012 | Liversidge |
| 8,512,295 B2 | 8/2013 | Evans et al. |
| 8,597,255 B2 | 12/2013 | Emmott et al. |
| 8,968,241 B2 | 3/2015 | Liversidge |
| 9,216,256 B2 | 12/2015 | Olson et al. |
| 9,233,213 B2 | 1/2016 | Olson et al. |
| 2002/0087180 A1 | 7/2002 | Searle et al. |
| 2003/0144632 A1 | 7/2003 | Hommann et al. |
| 2004/0019326 A1 | 1/2004 | Gilbert et al. |
| 2005/0085839 A1 | 4/2005 | Allen et al. |
| 2005/0222539 A1 | 10/2005 | Gonzales et al. |
| 2005/0273061 A1 | 12/2005 | Hommann et al. |
| 2006/0142691 A1 | 6/2006 | Trautman et al. |
| 2006/0167411 A1 | 7/2006 | Weston et al. |
| 2006/0189938 A1 | 8/2006 | Hommann et al. |
| 2006/0229569 A1 | 10/2006 | Lavi et al. |
| 2006/0270984 A1 | 11/2006 | Hommann et al. |
| 2006/0270985 A1 | 11/2006 | Hommann et al. |
| 2007/0111175 A1 | 5/2007 | Raven et al. |
| 2007/0173770 A1 | 7/2007 | Stamp |
| 2008/0154200 A1 | 6/2008 | Lesch |
| 2008/0228147 A1 | 9/2008 | David-Hegerich et al. |

* cited by examiner

SAFETY DEVICE FOR A PRE-FILLED SYRINGE AND INJECTION DEVICE

CROSS REFERENCE TO RELATED APPLICATIONS

The present application is a continuation of U.S. patent application Ser. No. 15/973,059, filed May 7, 2018, which is a continuation of U.S. patent application Ser. No. 15/097,712, filed Apr. 13, 2016, now U.S. Pat. No. 9,962,499, which is a continuation of U.S. patent application Ser. No. 13/807,043, filed Apr. 29, 2013, now U.S. Pat. No. 9,314,574, which is a U.S. National Phase Application pursuant to 35 U.S.C. § 371 of International Application No. PCDEP2011/060320, filed Jun. 21, 2011, which claims priority to European Patent Application No. 10168319.1, filed on Jul. 2, 2010. The entire disclosure contents of these applications are herewith incorporated by reference into the present application.

FIELD OF INVENTION

The present invention relates to safety devices that provide needle safety and more particularly to safety devices for pre-filled syringes. The safety device is adapted to avoid accidental needle pricks and needle injuries before, during and after an injection of a medication or drug contained in the pre-filled syringe. In particular, the safety device provides needle safety for a subcutaneous self-administrated injection or for an injection administered by a health-care professional. The present invention further relates to injection devices comprising a pre-filled syringe.

BACKGROUND

Pre-filled syringes that are filled with a selected dosage of a medication are well known injection devices for administering the medication to a patient. Safety devices for covering a needle of a pre-filled syringe before and after use are also well known. Typically, these devices comprise a needle shield that is either manually moved or moved by the action of a relaxing spring to surround the needle.

A different type of safety devices known in the state of the art solve the object of providing needle safety by arranging the pre-filled syringe movable relative to a body, whereas the pre-filled syringe is retracted into the body after the injection.

SUMMARY

It is an object of the present invention to provide an improved safety device for a pre-filled syringe.

It is a further object of the invention to provide an improved injection device comprising a pre-filled syringe that is safe to handle and in particular prevents accidental needle stick injuries.

The object is achieved by a safety device according to claim 1 and by an injection device according to claim 12.

Preferred embodiments of the invention are given in the dependent claims.

In the context of this specification, the terms distal and proximal are defined from the point of view of a person performing an injection. Consequently, a distal direction refers to a direction pointing towards the body of patient receiving an injection and a distal end defines an end of an element that is directed towards the body of the patient. Respectively, the proximal end of an element or the proximal direction is directed away from the body of the patient receiving the injection and opposite to the distal end or distal direction.

According to the invention, a safety device for a pre-filled syringe comprises a substantially cylindrical and hollow support body and a hollow needle shield slideably arranged relative to the support body. The support body comprises at least one resilient arm and the hollow needle shield or a needle shield assembly comprises at least one curved actuation ramp. The curved actuation ramp protrudes in a lateral direction perpendicular to a central axis of the safety device. The curved actuation ramp comprises a first lateral dimension at a proximal end of the needle shield and a second lateral dimension exceeding the first lateral dimension at a distal end of the needle shield. The resilient arm engages the curved actuation ramp when the needle shield is slid relative to the support body.

The curved actuation ramp gives the safety device a tapered shape that differs from typical designs of safety devices for pre-filled syringes. The safety device according to the present invention has a trumpet-like design that is in general not associated by a typical user with the unpleasant act of receiving an injection. The design of the safety device thus alleviates a possible fear of receiving an injection. This is particularly useful in the context of self-administered injections, as a fear of needles or injections might keep the patient from performing the injection properly.

According to a possible embodiment of the invention, the curved actuation ramp is integrated to the needle shield.

In an alternative embodiment of the invention, the curved actuation ramp is separate part connected to the needle shield. A needle shield assembly constitutes the needle shield and the curved actuation ramp.

According to a possible embodiment of the invention, the resilient arm acts as a spring means to bias the needle shield with respect to the support body in the distal direction and it is made from a plastics material. The safety device does not comprise any metallic part and is completely made from plastics materials, so that the safety device can be cost-efficiently manufactured in high quantities. The safety device is well suited in combination with disposable syringes and is disposed with the pre-filled syringe retained within the safety device after a first use.

Preferably, the resilient arm is integrally formed to the support body. The resilient arm acts as a biasing means integral with the support body. The safety device comprises only a few parts made from plastics materials, so that the production costs of the safety device are significantly reduced in comparison to typical safety devices that comprise regular metal springs.

The resilient arm is non-energized in a rest position and extends essentially parallel to the central axis and over a substantial axial length of the support body in the rest position. The resilient arm provides a simple mechanism for the biasing means of the safety device that is stressed and energized during use of the safety device.

According to another possible embodiment of the invention, the needle shield is movable with respect to the support body from an initial position to a retracted position and further to an advanced position. The needle shield protrudes the support body in the initial position and in the advanced position to surround a hypodermic needle of the pre-filled syringe retained within the safety device. The needle shield is substantially received within the support body in the retracted position.

According to yet another possible embodiment, the needle shield is made from an opaque plastics material. The hypodermic needle is hidden from the view of the patient before the injection by the needle shield that is retained in the initial position. This eases a possible fear of needles of the patient. The safety device is thus particularly suited for performing self-administered injections.

According to an alternative embodiment, the needle shield is made from a transparent plastics material A healthcare professional that uses the safety device thus can visually confirm the correct placement of the hypodermic needle penetrating the skin of the patient, even when the hypodermic needle is surrounded by the needle shield.

As the safety device is both suited for self-administered injections and injections carried out by a healthcare professional, the person referred to as the user or the patient may be one and the same person.

When the needle shield is moved from the initial position to the retracted position, the resilient arm engages the curved actuation ramp and travels along an outer edge of the curved actuation ramp. When the needle shield reaches the retracted position, the resilient arm is bent in the lateral direction in a way that corresponds to a curvature of the curved actuation ramp. The resilient arm thus gets stressed and energized to bias the needle shield in the retracted position. The resilient arm is stressed for a short time span during use of the safety device. This allows for the use of a plastics material prone to fatigue of material for the biasing means without having to restrict the reliability of safety device.

The resilient arm is in the rest position when the needle shield is in the initial position. Prior to use, the needle shield is retained in the initial position, so that the resilient arm is in its un-stressed rest position. A fatigue of material and/or a memory effect leading to a limited flexibility of the resilient arm is thus avoided even after prolonged periods of storage.

According to yet another possible embodiment of the invention, the curved actuation ramp is integral formed to the needle shield, so that the safety device only comprises a low number of parts to lower production costs.

According to yet another embodiment, the needle shield comprises a skin-contact flange that rests onto the skin of the patient during the injection of a medication contained in the pre-filled syringe. The skin-contact flange facilitates the correct placement of the hypodermic needle, so that in particular an unskilled user may perform a proper injection. Furthermore, the skin-contact flange is pressed towards the skin surface of the patient during the injection. The skin-contact flange comprises an increased surface area to spread the load and the injection may be comfortably carried out.

According to yet another possible embodiment, the needle shield comprises two laterally protruding curved actuation ramps that protrude opposite sides of the needle shield. This ensures that the biasing force exerted on the needle shield by the biasing arm is directed parallel to the central axis of the safety device. In particular, this prevents a jamming of the needle shield within the support body when the needle shield is moved from the retracted position to the advanced position by the action of the relaxing resilient arm.

The safety device comprises a substantially cylindrical outer body that is slideably arranged with respect to the support body. The outer body is slid with respect to the support body to expel the medication contained in the pre-filled syringe that is retained within the support body of the safety device. The outer body comprises at least one axial slot sized to receive the resilient arm and/or the curved actuation ramp. The resilient arm and/or the curved actuation ramp protrudes through the axial slot when the support body is received within the outer body at the end of the injection stroke.

An injection device comprises a pre-filled syringe and a safety device. The pre-filled syringe comprises a hypodermic needle attached to a distal end of the pre-filled syringe, a barrel with an inner cavity in fluid communication with the hypodermic needle and a piston fluid-tightly sealing a proximal end of the inner cavity. The piston is movable by actuating a piston rod protruding a proximal end of the barrel. The safety device for the pre-filled syringe comprises a substantially cylindrical and hollow support body and a hollow needle shield slideably arranged relative to the support body, The support body comprises at least one resilient arm. The needle shield comprises at least one curved actuation ramp protruding in a lateral direction perpendicular to a central axis of the safety device. The curved actuation ramp comprises a first lateral dimension at a proximal end of the needle shield and a second lateral dimension exceeding the first lateral dimension at a distal end of the needle shield. The resilient arm engages the curved actuation ramp when the needle shield is slid relative to the support body. The hypodermic needle protrudes the distal end of the support body and is surrounded by the needle shield in an initial position and/or in an advanced position.

The injection device comprising the pre-filled syringe and the safety device combines the aforementioned advantages and avoids inadvertent needle stick injuries before, during and after an injection delivering the medication beneath the skin of patient.

Details of the present invention are described hereinafter. However, it should be understood that the detailed description and the specific examples indicate possible embodiments of the invention and are given by way of illustration only. Various changes and modifications of the illustrated embodiments within the spirit and scope of the invention are appreciated by those skilled in the art.

BRIEF DESCRIPTION OF THE DRAWINGS

The present invention will be better understood from the detailed description given in the following. The accompanying drawings are given for illustrative purposes only and do not limit the scope of the present invention.

Corresponding parts are marked with the same reference symbols in all figures.

DETAILED DESCRIPTION

Figure 1:
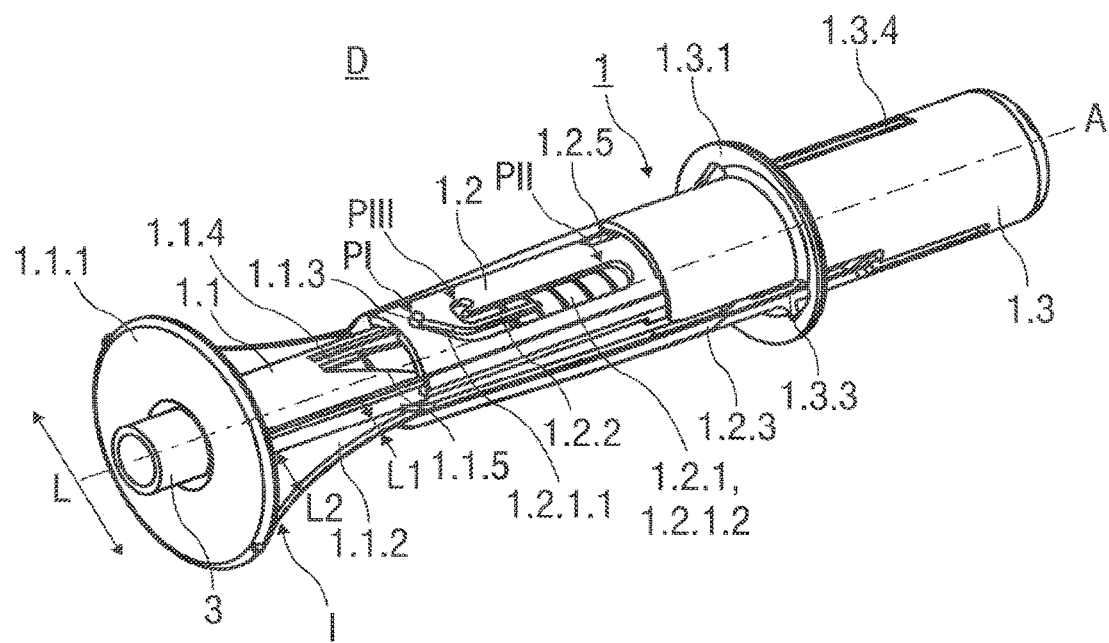
FIG. 1 shows a perspective view of an injection device with a safety device for a pre-filled syringe prior to use.

FIG. 1 shows an injection device D with a safety device 1 for a pre-filled syringe 2 as it would be presented to a user performing an injection. The safety device 1 comprises a hollow needle shield 1.1. The needle shield 1.1 is received within a substantially hollow support body 1.2, whereas the needle shield 1.1 is slida.ble with respect to the support body 1.2. Prior use of the safety device 1, the needle shield 1.1 is retained in an initial position 1, wherein the needle shield 1.1 protrudes the support body 1.2.

A circumferential skin-contact flange 1.1.1 is formed to the needle shield 1.1 at its distal end. The skin-contact flange 1.1.1 is adapted to be pressed against the skin of a patient and protrudes radial outwardly and perpendicular to a central axis A of the safety device 1. Edges of the skin-contact flange 1.1.1 that come into contact with the skin of the patient are rounded to avoid injuries, The skin-contact flange 1.1 has a central opening centred on the central axis A of the safety device 1. The skin-contact flange 1.1.1 is integral to the needle shield 1.1, or, alternatively, a separate part attached to the needle shield L1 that is made from a plastics material.

The needle shield 1.1 comprises two curved actuation ramps 1.1.2 that protrude two opposite sides of the needle shield in a lateral direction perpendicular to a central axis A of the safety device 1. Each curved actuation ramp 1.1.2 has a first lateral dimension L1 at a proximal end of the needle shield 1.1 and a second lateral dimension L2 at a distal end of the needle shield 1.1. The second lateral dimension L2 of the actuation ramp 1.1.2 exceeds the first lateral dimension L1 of the actuation ramp 1.1.2, The curved actuation ramp 1.1.2 is arranged with the needle shield 1.1 as one piece, or alternatively, a separate part made from a plastics material that is connected to the needle shield 1.1. In this alternative embodiment, a needle shield assembly comprises the needle shield 1.1 and the curved actuation ramp 1.1.2 connected to the needle shield 1.1.

A guide pin 1.1.3 is integrally formed to a flexible arm 1.1.4 of the needle shield 1.1. The flexible arm 1.1.4 extends in its rest position essentially parallel to the central axis A of the safety device 1. As illustrated in FIG. 1, the guide pin 1.1.3 protrudes radial outwardly into a guide track 1.2.1 formed into the substantially cylindrical support body 1.2. A trapezoid cut-out 1.1.5 is formed into the needle shield 1.1 adjacent to the flexible arm 1.1.4 to allow for a deflection and pivoting movement of the flexible arm 1.1.4. Prior to use of the safety device 1, the guide pin 1.1.3 is retained within an inclined section 1.2.1,1 of the guide track 1.2, in a start position Pt located at a distal end of the guide track 1.2.1, As the flexible arm 1.1.4 is in the rest position, the guide pin 1.1.3 is laterally non-biased in the start position PI. The inclined section 1.2.1.1 is oriented at an acute angle relative to the cylindrical axis A of the safety device 1.

The needle shield 1.1 is retained in an initial position I by the guide pin 1.1.3 being retained in a start position PI in the inclined section 1.2.1,1 of the guide track 1.2.1. The needle shield 1.1 is made from an opaque plastics material, so that a hypodermic needle 2.1 of the pre-filled syringe 2 retained within the safety device 1 is hidden from view of the patient before the injection.

Alternatively, the needle shield 1.1 is made from a transparent plastics material, so that a healthcare professional performing the injection may visually confirm the correct placement of the hypodermic needle 2.1 before penetrating the skin of the patient.

The guide pin 1.1.3 is prevented from leaving the start position PI by an interaction of several components of the safety device 1: Upon deflection, the flexible arm 1.1.4 biases the guide pin 1.1.3 in the lateral direction L back towards the start position PI. The guide pin 1.1.3 abuts the distal end of the inclined section 1.2.1.1 in the lateral direction L and distal direction.

The guide track 1.2.1 comprises a widened section 1.2.1.2 extending parallel to the central axis A of the safety device 1. A flexible separating wall 1.2.2 extends parallel to the central axis A and into the widened section 1.2.1.2 from a distal direction. The flexible separating wall 1.2.2 is integral part with the support body 1.2 and acts as a no-return feature preventing the guide pin 1.1.3 from returning to its start position PT after an injection stroke has at least partially been carried out. Furthermore, the flexible separating wall 1.2.2 guides the movement of the guide pin 1.1.3 within the guide track 1.2.1, so that the guide pin 1.1.3 is prevented to enter an end position PIII from the distal direction but allowed to enter from the proximal direction. The end position PIII is defined by a generally U-shaped indent between the distal and a proximal end of the guide track 1.2.1.

The support body 1.2 is made from a resilient plastics material. The support body 1.2 is slotted along a substantial longitudinal length parallel to the central axis A, so that two resilient arms 1.2.3 are formed to opposite sides of the support body 1.2. Each resilient arm 1.2.3 protrudes the support body 1.2 in a radial outward direction. The resilient ann 1.2.3 acts as a spring means of the safety device 1, whereas the resilient arm 1.2.3 biases the support body 1.2 and the needle shield 1.1 away from each other when these parts 1.1, 1.2 are slid relative to each other during the injection.

Alternatively, the resilient arms 1.2.3 may be separate plastics parts that are connected to each other by a collar that is retained within and affixed to the support body 1,2

The safety device 1 comprises an essentially cylindrical and hollow outer body 1.3 made from a plastics material with an open distal and a closed proximal end. The proximal end of the support body 1.2 is received within the open distal end of the outer body 1.3, whereas the outer body 1.3 is slidable with respect to the support body 1.2 in a distal direction to substantially receive the support body 1.2 inside the outer body 1.3.

A circumferential and outwardly protruding hand flange 1.3.1 is integrally formed to an exterior surface of the outer body 1.3 close to its distal end.

Furthermore, two opposing axial slots 1.3.3 are formed into opposite sides of the outer body 1.3 that receive the outwardly protruding resilient arms 1.2.3 and the curved actuation ramps 1.1.2 when the needle shield 1.1, the support body 1.2 and the outer body 1.3 are slid relative to each other during the injection.

Figure 7:
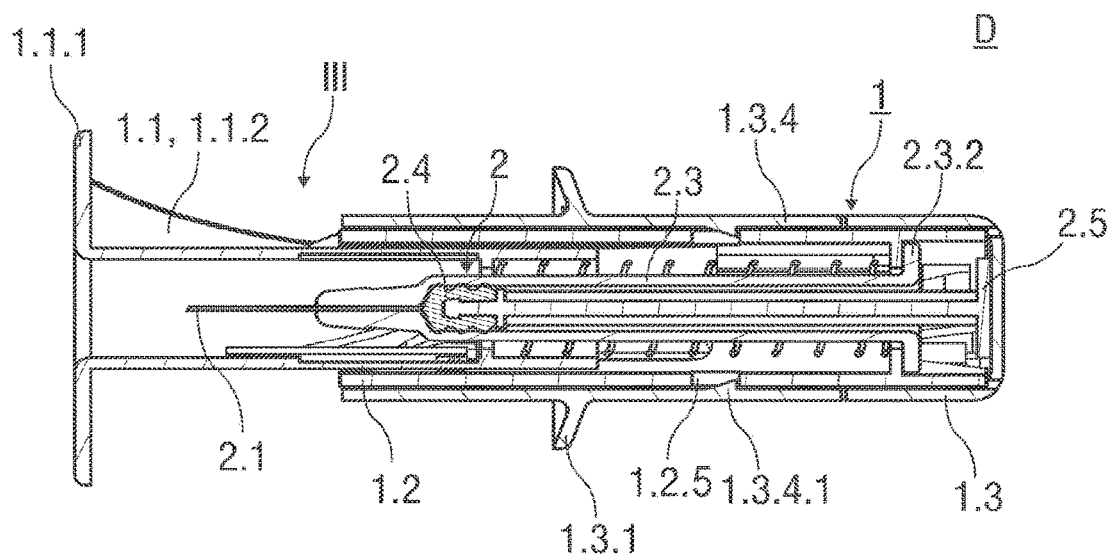
FIG. 7 shows a sectional view of an injection device with a safety device after an injection has been performed.

A clamp arm 1.3.4 is formed into the substantially cylindrical outer body 1.3 that is deflectable in the radial direction perpendicular to the central axis A. As best seen in FIG. 7, the clamp arm 1.3.4 comprises an inwardly protruding locking catch 1.3.4.1 that is sized to fit into a locking recess 1.2.5 formed into the support body 1.2 in proximity of a proximal end of the support body 1.2.

Figure 2:
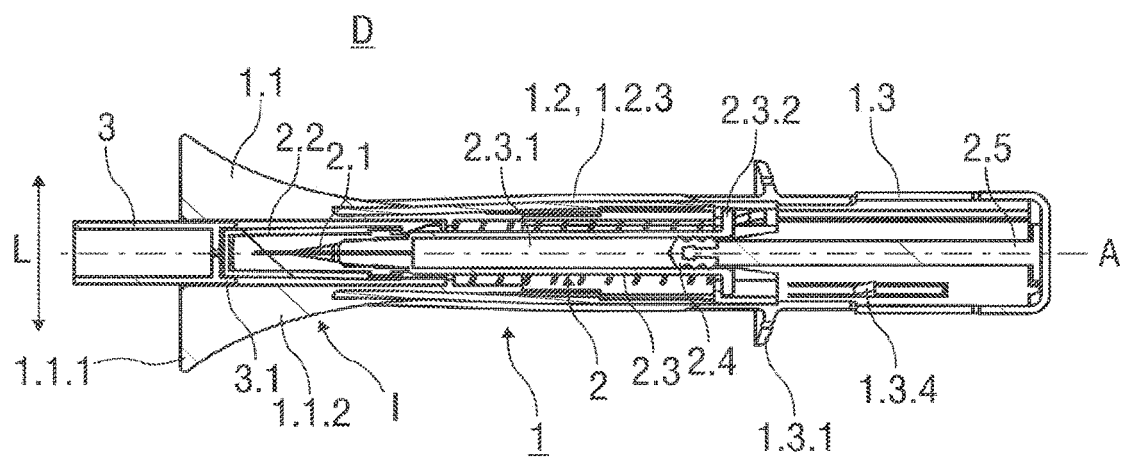
FIG. 2 shows a sectional view of the injection device with a safety device for a pre-filled syringe with a needle shield retained in an initial position.

The injection device D comprises the safety device 1 with the pre-filled syringe 2 retained within the support body 1.2. FIG. 2 shows the pre-filled syringe 2 received within the support body 1.2 that comprises a hypodermic needle 2.1 covered by a needle cap 2.2 frictionally affixed to a distal end of a barrel 2.3. The barrel 2.3 has an inner cavity 2.3.1 containing a medication. The inner cavity 2.3.1 is in fluid communication with the hypodermic needle 2.1. A proximal end of the inner cavity 2.3.1 is fluid-tightly sealed by a piston 2.4 that is connected to a piston rod 2.5. The piston 2.4 is movable in at least the distal direction by actuating the piston rod 2.5 protruding the barrel 2.3 in the proximal direction. The barrel 2.3 of the pre-filled syringe 2 comprises a barrel collar 2.3.2 that abuts a radial inwardly protruding inner surface of the support body 1.2 at its proximal end affixing the pre-filled syringe 2 to the support body 1.2.

Figure 6:
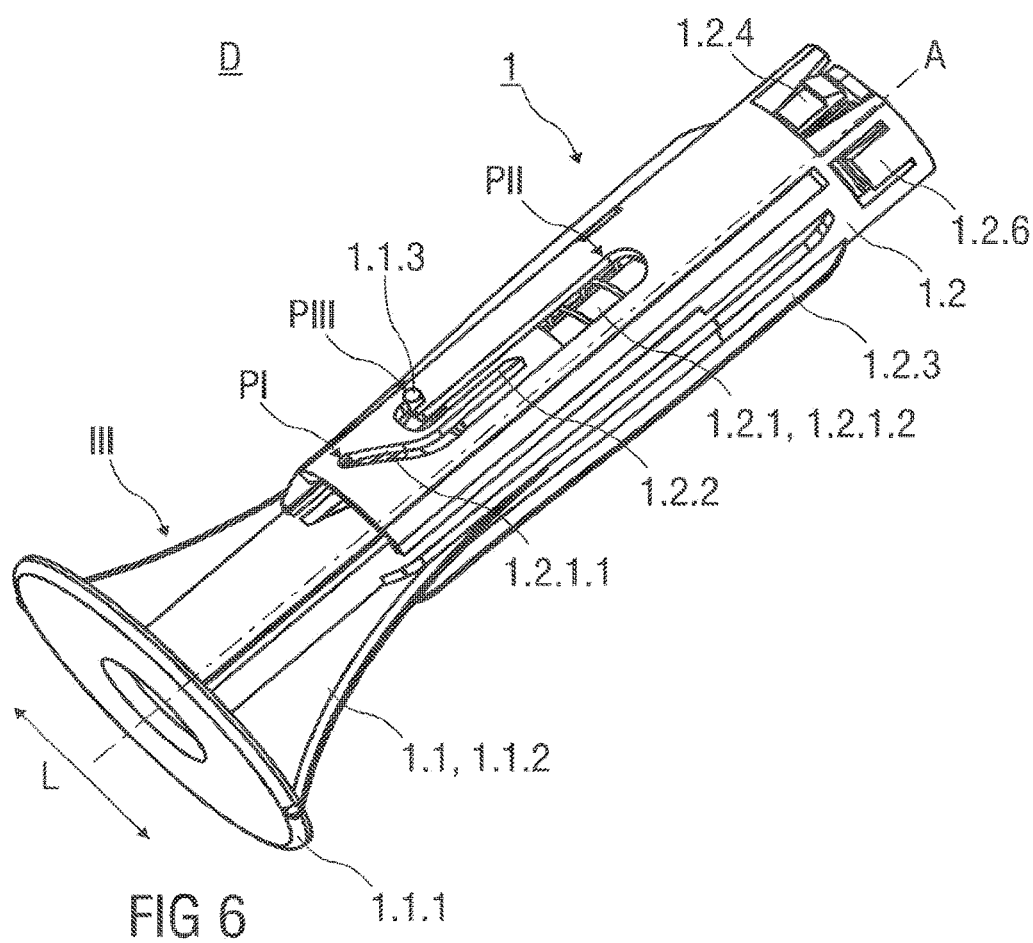
FIG. 6 shows a perspective view of a support body and a needle shield of a safety device, whereas the needle shield is retained in an advanced position.

With cross-reference to FIG. 6, it can be seen that the support body 1.2 comprises clips 1.2.6 that engage the barrel collar 2.3.2 to retain the pre-filled syringe 2 within the support body 1.2.

The pre-filled syringe 2 is retained within the support body 1.2, whereby the hypodermic needle 2.1 protrudes the support body 1.2 in the distal direction.

In the packaged state as shown in FIGS. 1 and 2, the hypodermic needle 2.1 is covered by needle cap 2.2 that is surrounded by the needle shield 1.1 prior to use of the injection device D. The needle cap 2.2 is preferably at least partially made from a plastics material like rubber. The width of the central opening of the skin-contact flange 1.1.1 corresponds to an outer diameter of the needle cap 2.2. A needle cap remover 3 is inserted into the central opening of the skin-contact flange 1.1.1 and protrudes the skin-contact flange 1.1.1 in a distal direction, so that the user can easily remove the needle cap 2.2 from the pre-filled syringe 2 by pulling the needle cap remover 3 in the distal direction. The needle cap remover 3 comprises clamp means 3.1 that clamp to a distal end of the needle cap 2.2.

Alternatively, the injection device D comprising the safety device 1 with the pre-filled syringe 2 retained therein is shipped and delivered to an end-user with a needle cap remover 3 attached to the distal end of the needle cap 2.2 retained within the safety device 1, so that the needle cap remover 3 protrudes the needle shield 1. tin the distal direction.

As shown in FIG. 2, a proximal end of the piston rod 2.5 abuts the closed distal end of the outer body 1.3, so that the piston 2.4 is movable in a distal direction by the distal displacement of the outer body 1.3 with respect to the support body 1.2, Alternatively, the piston rod 2.5 is connected to the outer body 1.3 or an integral to the outer body 1.3. This alternative embodiment has additional advantage of a low overall part count, so that manufacturing costs are reduced.

The needle shield 1.1 is in the initial position I surrounding the hypodermic needle 2.1 of the pre-filled syringe 2.

Figure 3:
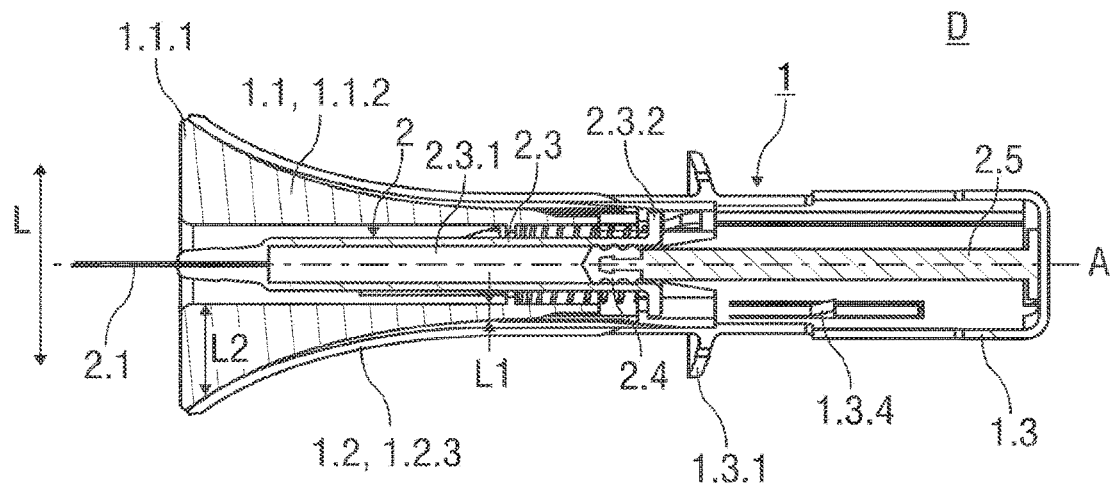
FIG. 3 shows a sectional view of the injection device with a safety device for a pre-filled syringe with a needle shield retained in a retracted position, whereas a resilient arm is stressed and energized.

FIG. 3 shows a sectional view of the injection device D with the safety device 1 at the beginning of an injection stroke. The needle shield 1.1 is in the retracted position wherein the needle shield 1.1 is substantially received within the support body 1.2. The hypodermic needle 2.1 distally protrudes the skin-contact flange 1.1.1 of the needle shield 1.1. The resilient arm 1.2.3 engaging the curved actuation ramp 1.1.2 is outwardly bent in the lateral direction L and is curved corresponding to the curvature of the curved actuation ramp 1.1.2. The resilient arm 1.2.3 is in a maximally stressed state to bias the needle shield 1.1 with respect to the support body 1.2 in the distal direction.

Figure 4:
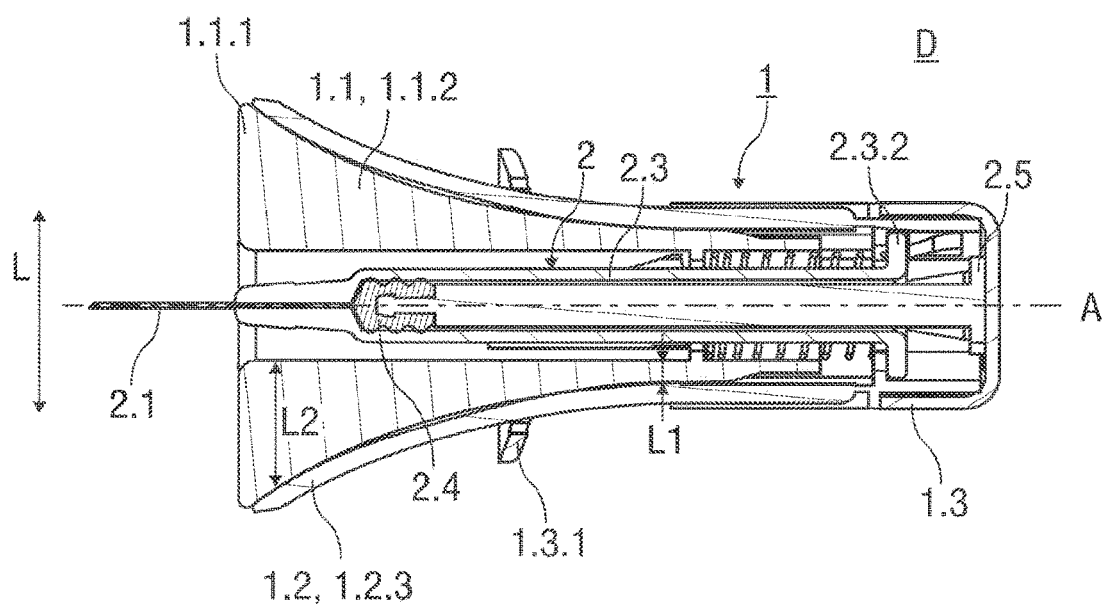
FIG. 4 shows a sectional view of the injection device with a safety device for a pre-filled syringe at the end of an injection stroke.

FIG. 4 shows a sectional view of the injection device D with the safety device 1 at the end of the injection stroke. The needle shield 1.1 is in the retracted position II, wherein the needle shield 1.1 is substantially received within the support body 1.2. The guide pin 1.1.3 that is integral to the needle shield 1.1 is in an intermediate position PII within the guide track 1.2.1 in proximity of a proximal end thereof. The intermediate position PII of the guide pin 1.1.3 within the guide track 1.2.1 corresponds to the retracted position II of the needle shield 1.1.

Figure 5:
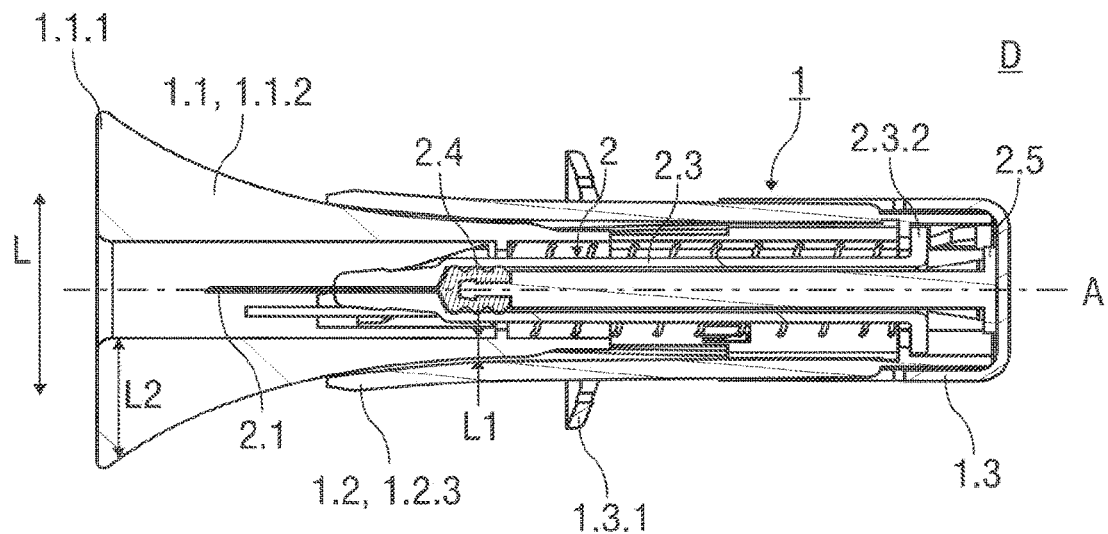
FIG. 5 shoes a sectional view of the injection device with a safety device with the needle shield retained in an advanced position.

FIG. 5 shows a sectional view of the injection device D with the safety device 1 after the injection of the medication. The needle shield 1.1 is in an advanced position li protruding distally from the support body 1.2, whereas the hypodermic needle 2.1 is surrounded by the needle shield 1.1 to avoid needle accidental needle injuries. The needle shield 1.1 is fixed to the advanced position III by the guide pin 1.1.3 being retained in the end position PIII.

The resilient arms 1.2.3 are in their rest position and extend substantially parallel to the cylindrical axis A. The support body 1.2 is substantially received within the outer body 1.3.

FIG. 6 shows a perspective view of the needle shield 1.1 retained with respect to the support body 1.2 in the advanced position III. The support body 1.2 comprises two clips 1.2.6 diametrical opposite to each other. The clips 1.2.6 are located near the proximal end of the support body 1.2 and clamp to the collar 2.3.2 of the pre-filled syringe 2 to affix the pre-filled syringe 2 to the support body 1.2, so that the pre-filled syringe 2 is firmly retained within the support body 1.2.

Two longitudinal recesses (not illustrated) are formed into the opposite sides of an inner surface of the outer body 1.3. The longitudinal recess extends over a substantial axial length of the outer body 1.3 and parallel to the central axis A. Each longitudinal recess receives a corresponding outward projection (not illustrated) formed to a proximal end of the support body 1.2. The outward projection moves within the longitudinal recess when the outer body 1.3 is slid relative to the support body 1.2 to perform the injection stroke, whereby a rotation of the outer body 1.3 relative to the support body 1.2 is prevented. Prior to use of the safety device 1, the outward projection abuts a distal end of the longitudinal recess to limit a proximal movement of the outer body 1.3 with respect to the support body 1.2.

FIG. 7 shows a sectional view of the safety device 1, whereas the plane section shown extends essentially perpendicular to the cross-section shown in FIG. 5. The piston 2.4 is fully depressed inside the barrel 2.3 of the pre-filled syringe 2. The support body 1.2 is received within the outer body 1.3 and locked to it, so that a re-usage of the safety device 1 is prevented. The inwardly protruding locking catch 1.3.4.1 formed to the clamp ann 1.3.4 latches to the corresponding locking recess 1.2.5 formed into the support body 1.2 to irreversibly lock the support body 1.2 with respect to the outer body 1.3.

FIGS. 8A to 8F show details of the guide track 1.2.1 formed into the support body 1.2 and the movement of the guide pin 1.1.3 within the guide track 1.2.1 during use if the safety device 1.

Figure 8A:
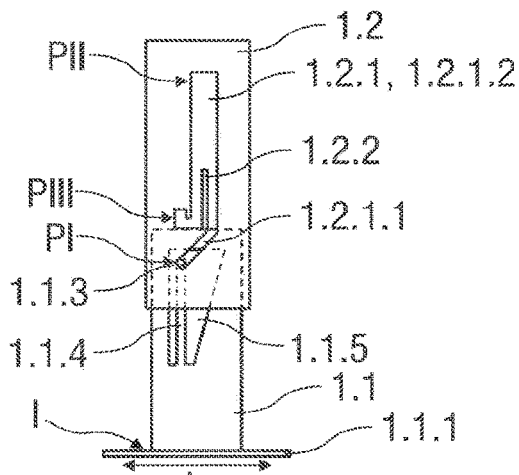
FIGS. 8A to 8F show details of a guide track and the movement of a guide pin within the guide track during use of the safety device.

As shown in FIG. 8A, the guide pin 1.1.3 is retained prior to the injection in the start position PI at the distal end of the inclined section 1.2.1.1 of the guide track 1.2.1, affixing the needle shield 1.1 to the initial position I. In the initial position I, the hypodermic needle 2.1 is surrounded by the needle shield 1.1.

The injection is carried out by orientating the central axis A essentially perpendicular to the skin of the patient, whereas the skin-contact flange 1.1.1 of the needle shield 1.1 rests on the skin surface of the patient and the proximal section of the outer body 1.3 proximal of the hand flange 1.3.1 is gripped by the user performing the injection. The hand flange 1.3.1 supports the hand of the user to carry out the injection stroke.

Figure 8B:
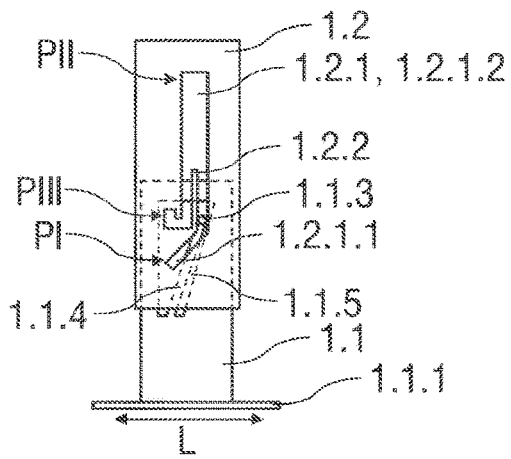

The injection is carried out in stages. In a first stage, the needle shield 1.1 is pushed inside the support body 1.2 in the proximal direction against the biasing force of the resilient arms 1.2.3 acting as spring means made from a plastics material. As illustrated in FIG. 8A and FIG. 8B, the guide pin 1.1.3 leaves its start position PI and moves along the inclined section 1.2.1.1 of the guide track 1.2.1. As the distal end inclined section 1.2.1.1 is oriented at an acute angle relative to the central axis A, the movement of the guide pin 1.1.3 causes the flexible arm 1.1.4 to become laterally deflected and stressed, so that the guide pin 1.1.3 is biased in a lateral direction L.

Figure 8C:
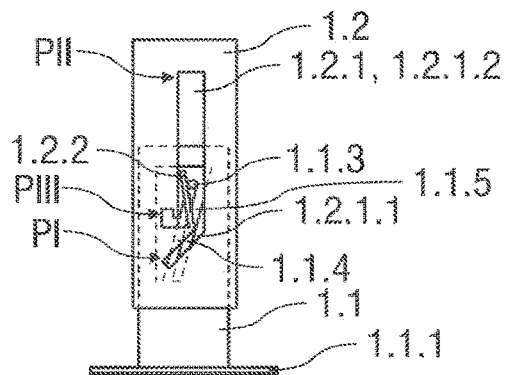

The guide pin 1.1.3 travels further along the guide track 1.2.1 in the proximal direction. As shown in FIG. 8C, the guide pin 1.1.3 enters the widened section 1.2.1.2 of the guide track 1.2.1 and abuts the flexible separating wall 1.2.2 in the lateral direction L. The flexible separating wall 1.2.2 is laterally deflected by a force exerted upon the flexible separating wall 1.2.2 by the stressed flexible arm 1.1.4. The elasticity of the flexible separating wall 1.2.2 is adapted to correspond to the elasticity of the flexible arm 1.1.4, so that the flexible separating wall 1.2.2 is deflectable by the deflected and stressed flexible arm 1.1.4.

The flexible separating wall 1.2.2 prevents the guide pin 1.1.3 from entering the end position PIII as the guide pin 1.1.3 enters the widened section 1.2.1.2 from the distal direction.

Figure 8D:
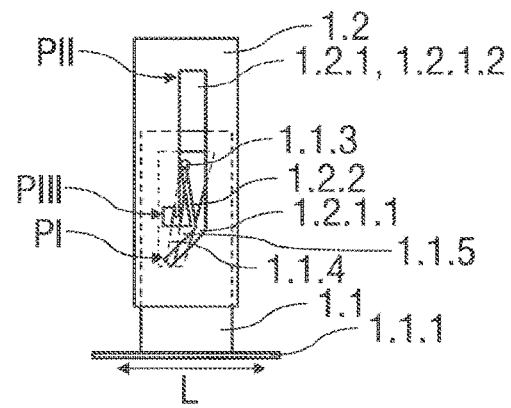

The guide pin 1.1.3 moves further proximally towards an intermediate position PII and reaches a proximal end of the flexible separating wall 1.2.2, as illustrated in FIG. 8D. At this point, the safety features of the safety device 1 are activated, as the flexible separating wall 1.2.2 relaxes and snaps back into its rest position substantially parallel to the central axis A. From now on, the end position PIII is accessible for the guide pin 1.1.3 to enter whereas the guide pin 1.1.3 is prevented to re-enter the start position PI. A subsequent removal of the safety device 1 causes the needle shield 1.1 and the guide pin 1.1.3 to advance distally, so that the needle shield 1.1 surrounds the hypodermic needle 2.1 of the pre-filled syringe in an advanced position III. The needle shield 1.1 is firmly retained in the advanced position III by the guide pin 1.1.3 being retained in the U-shaped indent of the guide track 1.2.1 defining the end position PIII, whereby a re-usage of the injection device D and/or the safety device 1 is prevented.

The flexible separating wall 1.2.2 has an axial dimension extending parallel to the central axis A and into the widened section 1.2.1.2 of the guide track 1.2.1. The axial dimension defines a minimal axial distance, the needle shield 1.1 has to be moved with respect to the support body 1.2 before the advanced position III is accessible for the needle shield 1.1 to enter. At the same time the safety features that prevent a re-usage of the safety device 1 are activated. Thus, an unintentional activation of the safety features of the safety device 1 is avoided, when the needle shield 1.1 is accidentally pushed distally by an axial length that is smaller than the minimal axial distance.

The safety device 1 generates an audible feedback indicating the activation of the safety features. The audible feedback can be generated by the flexible separating wall 1.2.2 snapping back into its rest position substantially parallel to the central axis A when the needle shield 1.1 is distally moved with respect to the support body 1.2 by an axial length that exceeds the minimal axial distance.

In order to inject the medication, the needle shield 1.1 is moved further in the proximal direction until it reaches the retracted position HI illustrated in FIG. 3, whereby the guide pin 1.1.3 is retained within the guide track 1.2.1 in the intermediate position P11. The resilient arms 1.2.3 are bent corresponding to the curvature of the curved actuation ramp 1.1.2. The resilient arms 1.2.3 are fully energized and stressed to bias the needle shield 1.1 with respect to the support body 1.2 in the distal direction. The user performing the injection presses the skin-contact flange 1.1.1 against the biasing force towards the skin surface of the patient, so that the hypodermic needle 2.1 penetrates the skin of the patient and the medication contained in the inner cavity 2.3.1 can be injected in the following second stage of the injection.

In the second stage, the outer body 1.3 moves with respect to the support body 1.1 in the distal direction. Simultaneously, the piston rod 2.5 interacting with the outer body 1.3 is actuated to move the piston 2.4 in the distal direction, whereby the medication contained in the inner cavity 2.3.1 is delivered through the hypodermic needle 2.1 and beneath the skin of the patient.

At the end of the injection stroke, the inwardly protruding locking catch 1.3.4.1 formed to the clamp ann 1.3.4 latches to the corresponding locking recess 1.2.5 formed into the support body 1.2 to irreversibly lock the support body 1.2. with respect to the outer body 1.3.

Figure 8E:
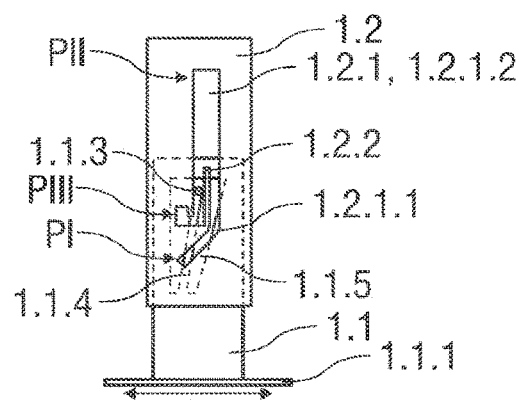

The injection device D comprising the safety device 1 with the pre-filled syringe 2 received therein is removed from the skin surface. The needle shield 1.1 immediately moves distally towards the advanced position III by the action of the relaxing resilient arms 1.2.3. As indicated in FIG. 8E, the guide pin 1.1.3 jointly moves with the needle shield 1.1 distally, whereby the guide pin 1.1.3 is guided by the flexible separating wall 1.2.2 towards the end position PIII.

Figure 8F:
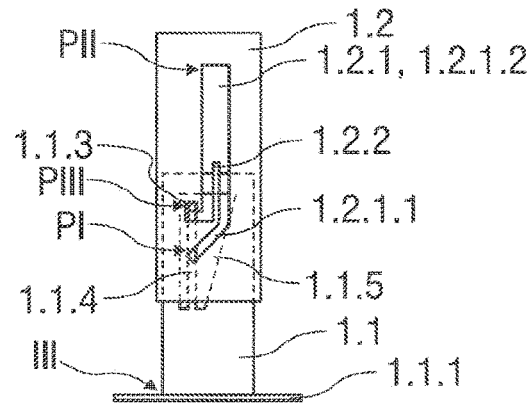

As indicated in FIG. 8F, the guide pin 1.1.3 enters the U-shaped indent defining the end position PIII of the guide track 2.1, whereby the flexible arm 1.1.4 relaxes to move the guide pin 1.1.3 laterally towards the end position PIII.

The guide pin 1.1.3 is firmly retained in the end position PIII, as the guide pin 1.1.3 abuts the U-shaped indent in the distal and in the lateral direction L. The flexible arm 1.1.4 is in the rest position, so that the guide pin 1.1.3 is laterally non-biased in the end. position PIII. A lateral movement of the guide pin 1.1.3 is prevented by the form of the U-shaped indent of the guide track 1.2.1 at the end position PIII and by the flexible arm 1.1.4. Thus, the guide pin 1.1.3 in the end position PIII irreversibly locks the needle shield 1.1 into the advanced position III after a single use of the safety device 1.

In one embodiment of the invention, the hypodermic needle 2.1 is hidden from the view of the patient throughout the injection.

The safety device 1 presented herein provides a simple mechanism to avoid needle stick injuries. The injection is carried out by a simple linear movement of the outer body 1.3 towards the skin of the patient, whereby the safety features that provide needle safety and prevent re-usage of the safety device 1 are automatically activated. The tapered shape and design of the safety device 1 with the curved actuation ramps 1.1.2 differs from typical designs of safety devices 1 for pre-filled syringes 2 to alleviate a possible fear of injections. The safety device 1, including the spring means, is exclusively made from plastics materials.

The invention claimed is:

1. A drug injection device comprising:
 a first body portion defining a cavity configured to receive a syringe, the first body portion comprising a first locking feature;
 a second body portion that is distally slideable with respect to the first body portion, the second body portion configured to receive part of the first body portion when the second body portion is slid distally with respect to the first body portion, the second body portion comprising a plunger extending distally from a proximal end portion of the second body portion, the plunger being configured to extend into the cavity of the first body portion when the second body portion is slid distally with respect to the first body portion, and the second body portion comprising a second locking feature configured to engage the first locking feature of the first body portion when the second body portion is slid distally a certain distance with respect to the first body portion, wherein axial movement of the first and second body portions relative to one another is limited when the first and second locking features are engaged;
 a needle shield that is slideable with respect to the first body portion between an extended position and a retracted position; and
 a needle cap remover that is configured to grasp a needle cap that covers a needle of the syringe when the syringe is disposed in the cavity of the first body portion.

2. The drug injection device of claim 1, wherein the needle shield is configured to slide into at least part of the first body portion, and the second body portion is configured to slide over at least part of the first body portion.

3. The drug injection device of claim 1, wherein one of the first and second locking features is a radially protruding catch and the other of the first and second locking features is a surface defining a recess configured to receive the radially protruding catch.

4. The drug injection device of claim 3, wherein the second locking feature is the radially protruding catch and the first locking feature is the surface defining the recess configured to receive the radially protruding catch.

5. The drug injection device of claim 4, wherein the radially protruding catch extends radially inward from a clamp arm of the second body portion.

6. The drug injection device of claim 5, wherein the surface defining the recess configured to receive the radially protruding catch is located along an outer surface of the first body portion.

7. The drug injection device of claim 1, wherein the second body portion comprises a clamp arm forming the second locking feature.

8. The drug injection device of claim 7, wherein the second locking feature is a catch that extends radially inward from the clamp arm.

9. The drug injection device of claim 7, wherein the first body portion comprises a recess forming the first locking feature.

10. The drug injection device of claim 1, wherein the first and second locking features are configured to engage one another when the second body portion has been slid distally a sufficient distance to deliver a dose of drug.

11. The drug injection device of claim 1, further comprising the syringe disposed in the cavity of the first body portion.

12. The drug injection device of claim 11, wherein the syringe contains a drug.

13. The drug injection device of claim 11, wherein the needle shield is configured to cover a needle of the syringe when the needle shield is in the extended position and is configured to expose the needle of the syringe when the needle shield is in the retracted position.

14. The drug injection device of claim 1, wherein the needle shield comprises a hollow tubular member.

15. The drug injection device of claim 1, wherein the needle shield comprises a distal flange portion configured to be pressed against skin of a patient during a drug injection.

16. The drug injection device of claim 15, wherein the distal flange portion of the needle shield extends radially outward from another portion of the needle shield.

17. The drug injection device of claim 1, wherein the needle cap remover comprises a portion configured to extend through a central opening of the needle shield.

18. The drug injection device of claim 17, wherein the central opening is in a distal flange of the needle shield.

19. The drug injection device of claim 1, wherein the needle cap remover is configured to remove the needle cap from the needle of the syringe when the needle cap is pulled distally.

20. The drug injection device of claim 1, wherein the plunger is configured to contact a stopper in the syringe when the syringe is disposed in the cavity of the first body portion and the second body portion is slid distally with respect to the first body portion.

21. The drug injection device of claim 20, wherein the plunger is configured to distally advance the stopper in the syringe to eject drug from the syringe when the syringe is disposed in the cavity of the first body portion and the second body portion is slid distally with respect to the first body portion.

22. The drug injection device of claim 1, wherein the plunger is integrally formed with the proximal end region of the second body portion.

23. The drug injection device of claim 1, wherein the second body portion defines a slot configured to receive a projection extending from a flexible arm of the first body portion.

24. The drug injection device of claim 23, wherein the projection extends radially outward from the flexible arm.

25. The drug injection device of claim 1, wherein the first body portion defines an opening and comprises a flexible arm extending axially within the opening.

26. The drug injection device of claim 25, wherein the flexible arm is configured to deflect laterally as the needle shield is slid with respect to the first body portion toward the retracted position.

27. The drug injection device of claim 25, wherein the needle shield defines an opening and comprises a flexible arm extending axially within the opening.

28. The drug injection device of claim 27, wherein the flexible arm of the first body portion is configured to engage the flexible arm of the needle shield such that both of the flexible arms deflect laterally as the needle shield is slid with respect to the first body portion toward the retracted position.

29. A drug injection device comprising:
- a first body portion defining a cavity configured to receive a syringe;
- a second body portion that is distally slideable with respect to the first body portion, the second body portion configured to receive part of the first body portion when the second body portion is slid distally with respect to the first body portion, the second body portion comprising a plunger extending distally from a proximal end portion of the second body portion, the plunger being configured to extend into the cavity of the first body portion when the second body portion is slid distally with respect to the first body portion,
- means for locking the second body portion to the first body portion when the first body portion is slid distally with respect to the first body portion;
- a needle shield that is slideable with respect to the first body portion between an extended position and a retracted position; and
- a needle cap remover that is configured to grasp a needle cap that covers a needle of the syringe when the syringe is disposed in the cavity of the first body portion.

30. The drug injection device of claim 29, wherein the needle cap remover comprises a portion configured to extend through a central opening of the needle shield, and the central opening is in a distal flange of the needle shield.

* * * * *

UNITED STATES PATENT AND TRADEMARK OFFICE
CERTIFICATE OF CORRECTION

PATENT NO. : 10,512,733 B2
APPLICATION NO. : 16/352398
DATED : December 24, 2019
INVENTOR(S) : Gareth Roberts et al.

Page 1 of 1

It is certified that error appears in the above-identified patent and that said Letters Patent is hereby corrected as shown below:

In the Specification

Column 1, Line 14, delete "PCDEP2011/060320," and insert -- PCT/EP2011/060320, --

Signed and Sealed this
Eighteenth Day of February, 2020

Andrei Iancu
*Director of the United States Patent and Trademark Office*